July 18, 1967 W. S. LEE Plant Pat. 2,752
JUNIPER PLANT
Filed May 23, 1966
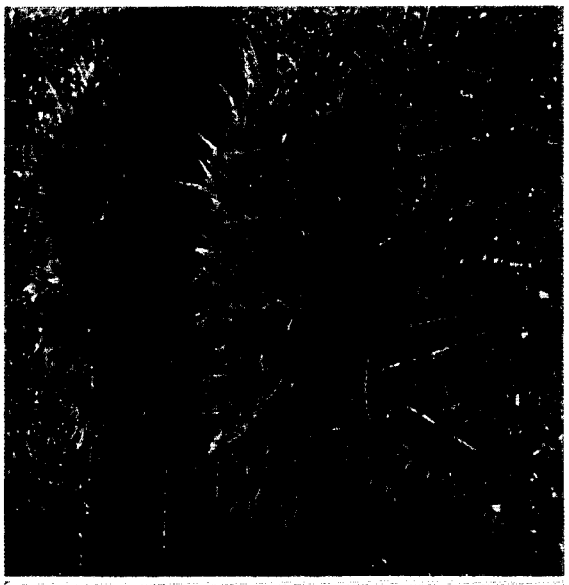
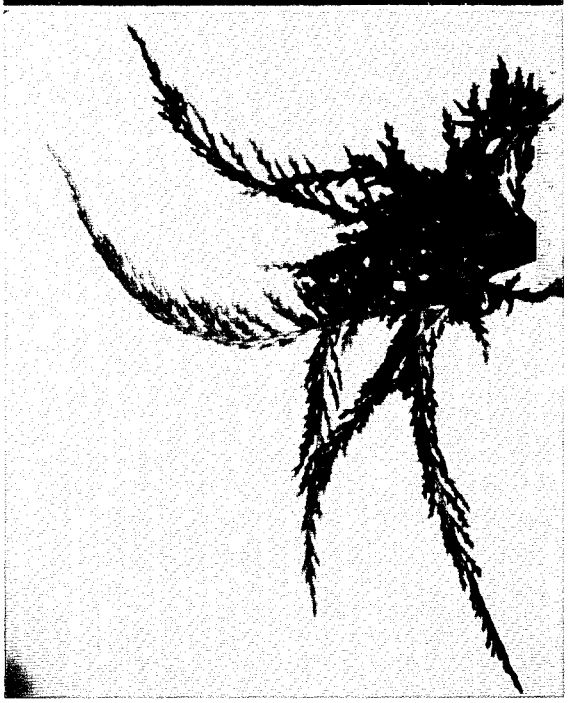
INVENTOR.
WALTER S. LEE,
By Edmond F. Shanahan.
ATTORNEY.

United States Patent Office

Plant Pat. 2,752
Patented July 18, 1967

2,752
JUNIPER PLANT

Walter S. Lee, Bellflower, Calif., assignor to Monrovia Nursery Co., Azusa, Calif., a corporation of California Filed May 23, 1966, Ser. No. 552,350
1 Claim. (Cl. Plt.—50)

The present invention relates to a new and distinct variety of the genus Juniperus.

The plant is characterized as to novelty by its compact, low habit of growth and by its distinctive blue-gray coloring. The specific known variety most like the new variety is *Juniperus horizontalis* Webberi, an unpatented variety; however, the present variety has distinct differences.

I discovered the original plant accidentally as a seedling, originating in 1953. The plant has been reproduced asexually by cutting and grafts. This plant does not reproduce from seed; seedlings revert to the variety found in *Juniperus horizontalis* generally.

The new variety is shown in full color in the accompanying composite illustration. A detailed description of the new variety follows.

*The plant*

Parentage: Chance seedling resulting from open pollenization.

*Pollen parent.*—Unknown.

*Seed parent.*—*Juniperus horizontalis.*

Growth: The plant is remarked for its compact, low habit of growth. The plant is densely branched, all branches being clothed with foliage. Oldest plants are now 7 years old, and at present, are approximately six inches in height, with a spread of nearly 3 feet.

Branches: The new growth of the branches is blue-gray in color, shading to a light tan and then to a reddish-brown with maturity.

Growth habit: Vigorous growth, and does not tend to mound, in contrast with the variety *Juniperus horizontalis* Webberi, which it most resembles. It will be noted from the accompanying illustrations that the center of the plant is covered with foliage and that no bare branches or stems show. No artificial handling or pruning has been practiced on the plant to make it grow low and prostrate.

Foliage: The foliage is soft and feathery. No scale-like imbricated foliage has been noted on any of the present plants.

Shape and arrangement: Leaves are oppositely arranged, densely crowded on branchlets, subulate (awl-like) on both new and mature growth.

Color: The plant retains its blue-gray color throughout the fall and winter months with very little of the bronze-purple coloring which usually characterizes most of the *Juniperus horizontalis* varieties.

Flower: No flower or cones have been noted, and it is not known whether the plants are pistillate or staminate.

I claim:

A new and distinct variety of juniper plant, substantially as herein described and illustrated, and characterized particularly as to novelty by its compact, low habit of growth and by its distinctive blue-gray coloring.

No references cited.

ABRAHAM G. STONE, *Primary Examiner.*

ROBERT E. BAGWILL, *Examiner.*